United States Patent [19]
Kadowaki et al.

[11] Patent Number: 5,544,217
[45] Date of Patent: Aug. 6, 1996

[54] MOBILE MEDICAL X-RAY APPARATUS

[75] Inventors: Toshio Kadowaki; Hajime Takemoto; Shojiro Yamaguchi, all of Kyoto, Japan

[73] Assignee: Shimadzu Corporation, Kyoto, Japan

[21] Appl. No.: 218,207

[22] Filed: Mar. 25, 1994

[30] Foreign Application Priority Data

Mar. 31, 1993 [JP] Japan .................................. 5-021648 U

[51] Int. Cl.$^6$ ...................................................... A61B 6/00
[52] U.S. Cl. ........................... 378/198; 378/193; 378/197
[58] Field of Search ...................................... 378/193, 195, 378/196, 197, 198

[56] References Cited

U.S. PATENT DOCUMENTS

| | | | |
|---|---|---|---|
| 4,715,057 | 12/1987 | Hahn et al. | 378/197 |
| 4,802,197 | 1/1989 | Juergens | 378/197 |
| 4,989,229 | 1/1991 | Negrelli et al. | 378/198 |
| 5,086,447 | 2/1992 | Siczek et al. | 378/197 |

*Primary Examiner*—David P. Porta
*Attorney, Agent, or Firm*—Majestic, Parsons, Siebert & Hsue

[57] ABSTRACT

A mobile medical X-ray apparatus has the entire weight of its X-ray source and X-ray detector as well as their supporting arm supported by a vertically movable support column on a mobile table. A lever and a member for supporting a normally compressed spring are attached to the table rotatably, and they are also connected to each other rotatably with respect to each other around a connector shaft such that the force of the spring tends to rotate the lever in the direction of causing the support column to move upward. The spring constant of the spring and the relative positions of the lever and the spring-supporting member are determined such that the support column can be moved manually upward or downward.

8 Claims, 2 Drawing Sheets

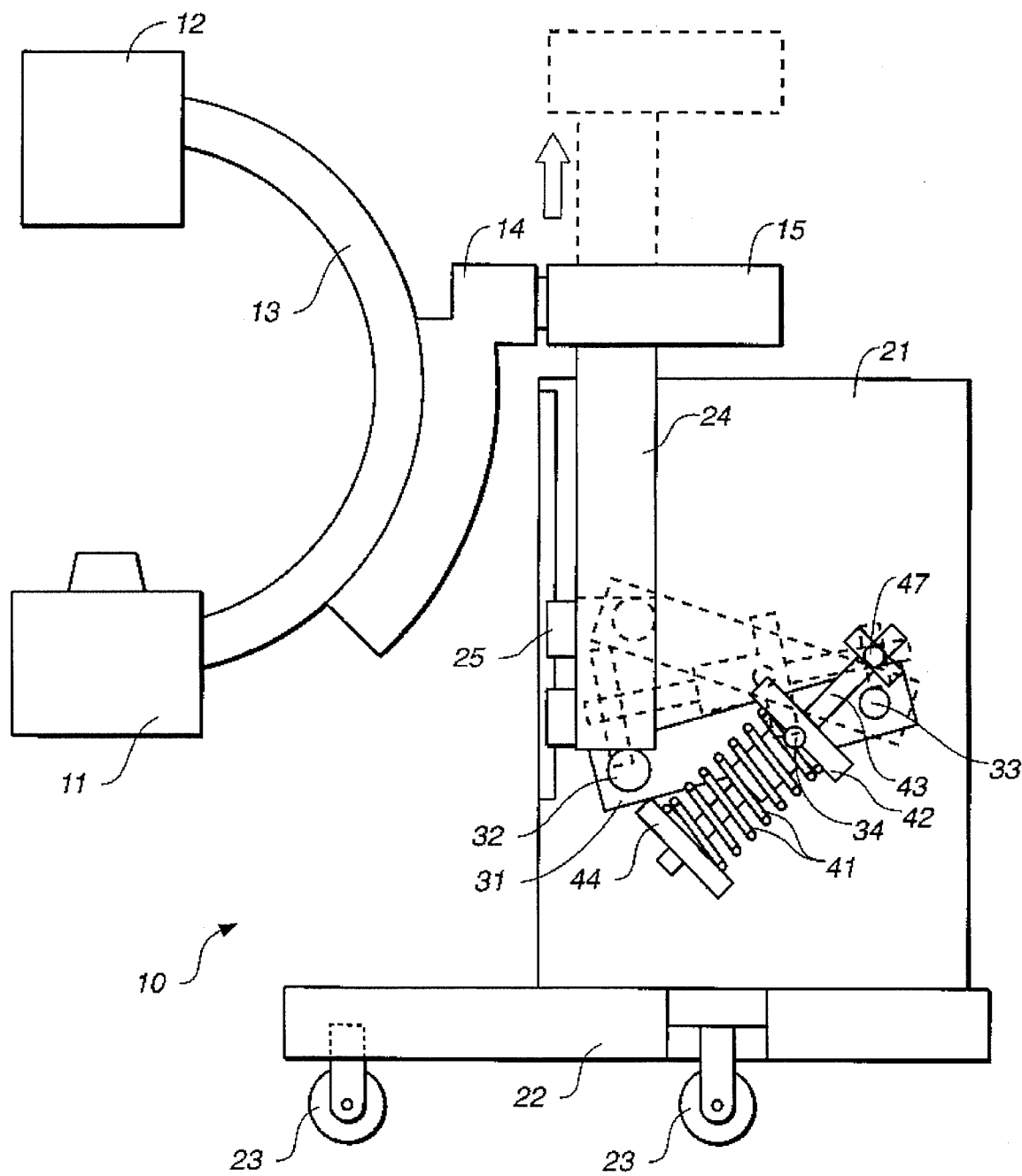
FIG._1

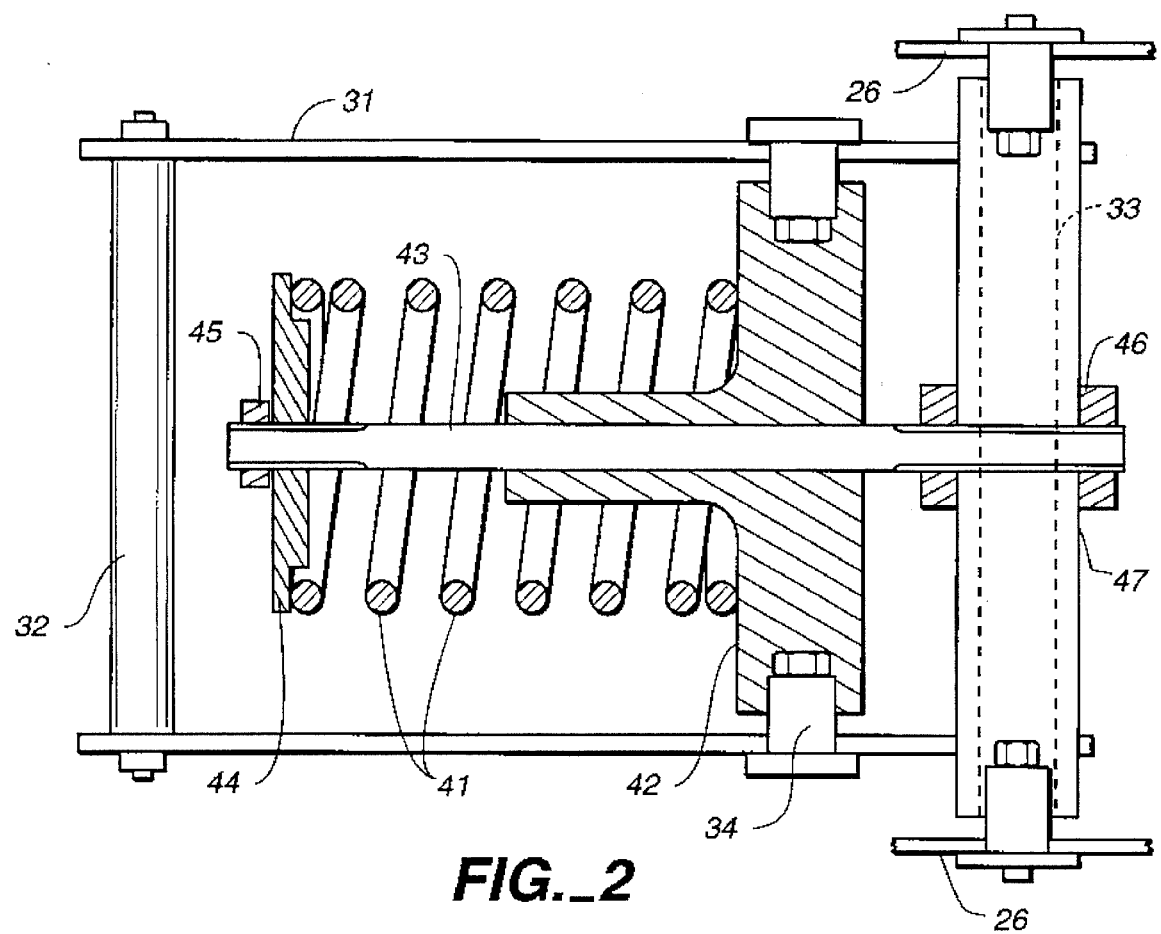
FIG._2
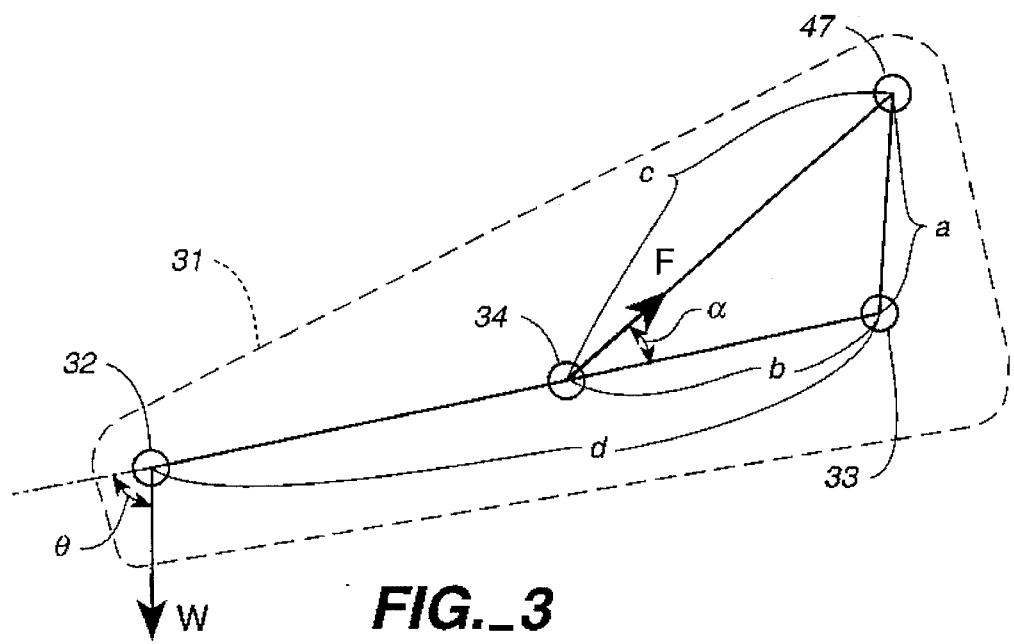
FIG._3

1

MOBILE MEDICAL X-RAY APPARATUS

BACKGROUND OF THE INVENTION

This invention relates to a mobile medical X-ray apparatus and, more particularly, to an X-ray apparatus of a kind carried on a mobile table.

A mobile X-ray apparatus of this kind has been disclosed, for example, in Japanese Utility Model Publication Jikkai 2-55919, characterized as having an X-ray source and an X-ray detector supported at both ends of a C-shaped arm held by a holder attached to a support column which is vertically moveable with respect to a wheeled table such that the heights of the X-ray source and the X-ray detector can be freely and conveniently adjusted. A spring is provided such that its force will balance the total weight of the components supported by the support column for vertically moving the C-arm holder, the X-ray source and the X-ray detector such that their heights can be adjusted without exerting a strong force. An apparatus thus structured, however, requires a large number of components for balancing and varying the directions of the forces since ropes and pulleys are used to balance the weight of the apparatus components with the force of the spring. Moreover, the mechanism is complicated and takes up a large space. As a result, some of these additional components must be placed inside the base part of the mobile table although this base part should preferably be reserved for a better use such as for housing the steering mechanism. If this cannot be done, a so-called rear wheel steering mechanism may have to be incorporated although it is not an ideal mechanism for such a medical apparatus from the point of view of operability.

SUMMARY OF THE INVENTION

In view of the above, it is an object of this invention to provide an improved kind of mobile medical X-ray apparatus which does not require a large number of components for a weight balancer for freely adjusting the heights of the X-ray source and the X-ray detector.

It is another object of the invention to provide such a mobile X-ray apparatus which can be made compact.

It is still another object of the invention to provide such a mobile X-ray apparatus with improved operability, having its steering mechanism stored inside the base part of its mobile table.

A mobile X-ray apparatus embodying the present invention, with which the above and other objects can be accomplished, may be characterized as comprising a lever, which is rotatably supported by a mobile table and serves to push up a vertically moveable column supporting an X-ray source and an X-detector, and a spring which is supported by a holder rotatably attached to the mobile table and supplies a lifting force to the lever.

With an apparatus thus formed, the force of the spring tends to rotate the lever in the direction of lifting the support column together with the X-ray source and the X-ray detector attached thereto, having the total weight of the support column balanced with the force of the spring. This makes it possible to move the X-ray source and the X-ray detector upward and downward to thereby adjust their heights without exerting a large force from outside. Since this force-balancing mechanism is comprised only of a lever, a spring, a spring holder and shafts for supporting and connecting them, the total number of components is relatively small and hence can be formed compactly. In other words, an apparatus according to this invention does not occupy a large space, and since the steering mechanism can be placed entirely inside the base part of the mobile table, the operability of the apparatus as a whole is also improved.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIG. 1 is a schematic side view of the a mobile medical x-ray apparatus embodying the present invention;

FIG. 2 is a plan view of a portion of the apparatus of FIG. 1 including the lever, the spring and the parts which move together therewith; and FIG. 3 is a drawing for showing the relationship between the forces acting on the lever of FIGS. 1 and 2.

DETAILED DESCRIPTION OF THE INVENTION

FIG. 1 shows schematically a mobile medical X-ray apparatus 10 embodying the present invention. An X-ray source 11 and an X-ray detector 12 are attached to the opposite ends of a so-called C-arm 13, which is a generally C-shaped arcuate member and is itself supported by an arm holder 14 so as to be able to slide thereon along the direction of its C-shaped curvature, thereby adjustably changing the relative angular direction of the X-ray detector 12 with respect to the X-ray source 11. The arm holder 14 is secured to a slide arm 15, which is supported at the top of a vertically elongated support column 24 so as to be horizontally slidable with respect to the latter.

The support column 24 is itself supported by a mobile table 21 by way of a vertically extending guide member 25 so as to be slidable vertically upward or downward, guided thereby. The mobile table 21 has a base 22 provided with wheels 23. Some of these wheels 23 are adapted to swivel around like a caster so as to facilitate the movement of the table 21.

With reference next both to FIGS. 1 and 2 simultaneously, there is a lever 31 rotatably supported around a horizontally extending lever shaft 33 which is attached to side walls 26 of the table 21. A column-supporting shaft 32 for supporting the support column 24 is attached to the lever 31 near an opposite end of the lever 31 away from the lever shaft 33 such that the bottom of the support column 24 rests thereon and a vertically downward force from the support column 24 is communicated to the lever 31 through this column-supporting shaft 32. There is also a spring rod 43 supporting a spring 41 therearound and fastened by a nut 46 to another horizontally extending rod-supporting shaft 47 which is rotatably supported by the side walls 26 of the table 21 parallel to and vertically above the lever shaft 33. The spring 41 is held between a spring seat 44 fastened by a nut 45 to the tip of the spring rod 43 distal from the rod-supporting shaft 47 and a spring holder 42 which is slidable longitudinally along the spring rod 43. The spring holder 42 and the lever 31 are connected to each other rotatably with respect to each other through a connector shaft 34 which not only is parallel to the lever shaft 33 and the rod-supporting shaft 47 but also lies in the plane determined by the lever shaft 33 and the column-supporting shaft 32 such that, as the spring rod 43 is rotated around the rod-supporting shaft 47, say, to a raised position indicated by dotted lines in FIG. 1, the lever 31 is caused to rotate around the lever shaft 33, thereby raising the support column 24 as indicated by an arrow. The natural length of the spring 41 is equal to the distance between the spring seat 44 and the rod-supporting shaft 47. In other words, the spring 41 is normally in a compressed state and exerts a force towards the rod-supporting shaft 47 to the lever 31 through the connector shaft 34. Thus, the force of the spring 41 tends to rotate the lever 31 in the clockwise direction (with respect to FIG. 1) and to raise the support column 24 through the column-supporting shaft 32.

Next, the balancing of the forces acting on the lever 31 will be analyzed with reference to FIG. 3. As shown in FIG. 3, there are two forces W and F contributing to a torque to the lever 31 around the lever shaft 33, W being the vertical force from the support column 24 exerted through the column-supporting shaft 32 and F being the force of the normally-compressed spring 41 in the direction of its extension (that is, towards the rod-supporting shaft 47). For the convenience of the following analyses, the fixed distances from the lever shaft 33 of the rod-supporting shaft 47, the connector shaft 34 and the column-supporting shaft 32 will be respectively denoted as a, b and d, and the distance between the rod-supporting shaft 47 and the connector shaft 34 as c when the angle made by the line segment connecting the lever shaft 33 and the column-supporting shaft 32 is $\theta$ from the vertical direction and e from the line segment connecting the connector shaft 34 and the rod-supporting shaft 47, as indicated in FIG. 3. Since the net torque on the lever 31 around the lever shaft 33 must be zero, $$bF\sin\alpha = dW\sin\theta.$$

Since the distance c represents also the length by which the spring 41 is compressed from its natural length, the force F exerted by the spring 41 is related to the distance c by $F=kc$ if k is the spring constant of the spring 41. The three variables c, $\alpha$ and $\theta$, however, are related as follows:

$$c\sin\alpha = a\sin\theta.$$

Thus, if these equations are combined together, the angles $\alpha$ and $\theta$ are cancelled out and there remains the relationship:

$$k=Wd/ab.$$

In other words, if the spring constant k is determined accordingly, the weight W on the support column 24 is always in equilibrium with the force F of the spring 41, independently of the vertical position of the support column 24. In still other words, the total weight of the X-ray source 11, the X-ray detector 12, the C-arm 13, the arm holder 14, the slide arm 15 and the support column 24 is supported by the column-supporting shaft 32 of the lever 31 which rotates by the force of the spring 41. As a result, these heavy components can be moved upward or downward manually with ease. The mechanism including the lever 31 and the spring 41 is simple and compact, without taking up a large space. Consequently, the base 22 can be used for other purposes, and prior art wheels and steering means can be used adequately for easy maneuverability.

In summary, the present invention provides a mobile medical X-ray apparatus which can be manually operated. As briefly summarized above, the C-arm 13 can be manually moved along the arcuate arm holder 14, and this means that the direction of the X-ray beam from the X-ray source 11 to the X-ray detector 12 can be adjusted easily by hand. The operator can also move the slide arm 15 manually. According to the present invention, furthermore, even the raising and lowering of the support column 24 can be effected manually. With prior art apparatus, by contrast, the raising and lowering of the support column are usually done by a motor, but such a motorized apparatus will continue to move even if the X-ray source, for example, has collided and stuck with the examination table. According to the present invention, all movements of the apparatus can be effected manually, and hence its safety record can be significantly improved.

Although the present invention has been described above with reference to only one example, the illustrated example is not intended to limit the scope of the invention. Details of the connecting mechanisms between the spring 41 and the lever 31, for example, may be varied, depending on the circumstances, within the general scope of this invention. In summary, the present invention discloses a mobile medical X-ray apparatus, characterized as using a mechanism including a spring and a lever to support the entire weight of the support column inclusive of the weight of the X-ray source and the X-ray detector supported thereby, such that the number of components is reduced and the apparatus can not only be made compact but also be easily operated.

What is claimed is:

1. A mobile medical X-ray apparatus comprising:
   a mobile table;
   a support column supported by said table and vertically movable with respect thereto;
   an X-ray source and an X-ray detector supported by said support column;
   a spring supporting member supported by said mobile table rotatably;
   a spring which is expandably and compressibly supported by said spring supporting member; and
   a lever which is attached to said table rotatably around a lever shaft such that the force of said spring tends to rotate said lever and to thereby push said support column upwards;
   said spring supporting member comprising:
      a rod;
      a spring seat to which are fastened one end of said spring and one end of said rod;
      a spring holder which is slidable longitudinally along said rod and is rotatably attached to said lever through a connector shaft and to which the other end of said spring is fastened; and
      a rod-supporting shaft which is rotatably supported by said table and is fastened to the other end of said rod.

2. The X-ray apparatus of claim 1 wherein said rod-supporting shaft is parallel to and disposed vertically above said lever shaft.

3. The X-ray apparatus of claim 1 further comprising a column supporting means attached to said lever for supporting said support column.

4. The X-ray apparatus of claim 3 wherein said connector shaft is parallel to said level shaft and lies in the plane defined by said level shaft and said column supporting means.

5. A mobile medical X-ray apparatus comprising:
   a mobile table;
   a support column supported by said table and vertically movable with respect thereto;
   an X-ray source and an X-ray detector supported by said support column;
   a spring supporting member supported by said mobile table rotatably;

a spring which is expandably and compressibly supported by said spring supporting member; and a lever which is attached to said table rotatably around a lever shaft such that the force of said spring tends to rotate said lever and to thereby push said support column upwards;

said spring supporting member comprising:

a rod;

a spring seat to which are fastened one end of said spring and one end of said rod;

a spring holder which is slidable longitudinally along said rod and is rotatably attached to said lever through a connector shaft and to which the other end of said spring is fastened; and a rod-supporting shaft which is rotatably supported by said table and is fastened to the other end of said rod, the natural length of said spring being equal to the distance between said spring seat and said rod-supporting shaft, the spring constant of said spring is such that the torque of the force of said spring around said lever shaft and the torque of the force from said support column to said lever around said lever shaft substantially cancel each other independently of the vertical position of said support column.

6. The X-ray apparatus of claim 5 wherein said rod-supporting shaft is parallel to and disposed vertically above said lever shaft.

7. The X-ray apparatus of claim 6 further comprising a column supporting means attached to said lever for supporting said support column.

8. The X-ray apparatus of claim 7 wherein said connector shaft is parallel to said level shaft and lies in the plane defined by said level shaft and said column supporting means.

* * * * *